United States Patent [19]

Bruns et al.

[11] Patent Number: 5,759,865

[45] Date of Patent: Jun. 2, 1998

[54] COMBINATORIAL PROCESS FOR SYNTHESIZING AZETIDINONE ANALOGS

[75] Inventors: Robert F. Bruns; Michael O. Chaney, both of Carmel; Robin D. Cooper, Indianapolis; David C. Hunden, Carmel; Gary A. Koppel; Jeffrey J. Skelton, both of Indianapolis, all of Ind.

[73] Assignee: Eli Lilly and Company, Indianapolis, Ind.

[21] Appl. No.: 433,115

[22] Filed: May 3, 1995

[51] Int. Cl.[6] .......................... G01N 33/543; A61K 38/00
[52] U.S. Cl. .......................... 436/518; 436/524; 436/526; 436/528; 530/333

[58] Field of Search ........................... 436/528, 524, 436/526; 530/333, 334, 335

[56] References Cited

U.S. PATENT DOCUMENTS 5,510,240  4/1996  Lam et al. .......................... 435/7.1

*Primary Examiner*—Ponnathapura Achutamurthy
*Attorney, Agent, or Firm*—Daniel W. Collins; Roger S. Benjamin; David E. Boone

[57] ABSTRACT

This invention relates to a combinatorial process for synthesizing a library of azetidinone peptide-like compounds. The compounds are synthesized as mixtures from a common azetidinone intermediate. The compounds are biologically active as inhibitors of the Vasopressin (V1a) receptor.

13 Claims, No Drawings

COMBINATORIAL PROCESS FOR SYNTHESIZING AZETIDINONE ANALOGS

BACKGROUND OF THE INVENTION

Pharmaceutical research and development expenses account for the largest outlay of capital in the industry. Most recent studies indicate that the cost to discover and develop a drug candidate which is eventually brought to market is roughly four hundred million dollars. Equally daunting is the time required to finally launch the product—roughly eleven years is the average time lag, measured from the first discovery of the novel compound.

Conventional methods of synthesis are to "blame" for the inordinate costs and delays of drug discovery research. Prior methods emphasized the synthesis of individual compounds for activity testing, followed by development of analogs in the event of a successful result (or "hit") in an effort to develop a thorough structure—activity relationship (SAR) and determine the most likely candidate for lead compound status.

This synthesis of individual compounds is the most expensive and time consuming phase of discovery research. Based upon the principles of "rational design", research chemists would synthesize hundreds of analogs of high purity for screening in order to fully develop the SAR. Although this rational design method worked better than its predecessor, the hit or miss random approach, the limitations of manual synthesis, coupled with the desire for high purity compounds at this initial phase of discovery, considerably slowed the development process.

The need for more rapid and less expensive discovery research is critical in the ever-evolving industry of drug development. It has become all too clear that reliance on the old paradigms of individual compound synthesis, followed by SAR development, is a slow road to oblivion. To compete in the 1990's and in the future, drug development companies must meet the challenge of rapidly developing new and innovative medicines, and in a manner which minimizes the research costs.

The currently accepted method of generating large numbers of compounds, referred to generically as "libraries", has been known in some form since the early 1960's. For nearly thirty years, the only efforts at library generation were in the peptide synthesis field. Even today, the majority of libraries generated by parallel synthesis methods are peptide or peptide-like compounds.

The parallel synthesis of peptide libraries carries advantages and disadvantages. Among the obvious advantages are the ability to theoretically generate huge numbers of compounds in a very short time period. Automated peptide synthesizers can provide for the creation of a theoretical number of peptides which increases exponentially as the number and variety of amino acid building blocks is increased. Examples of the numbers of peptides which are theoretically formed may be viewed in any of a number of prior art references, in both patents and publications.

Disadvantages of peptides include poor oral availability and short half life, which significantly reduces the chance that a lead compound will be developed much further than the initial phase. Further, the generation of huge libraries includes the synthesis of (theoretically) thousands of compounds in each vessel. Although a number of methods and devices have been suggested to assist in identification of individual compounds, the problem remains—identification of the specific active compound (or in some cases, combination of compounds) is extremely difficult and in some cases even more expensive and time-consuming than traditional methods.

Parallel synthesis of "small" molecules (non-oligomers with a molecular weight of 200–1000) was rarely attempted prior to 1990. F. Camps. et. al., Annaks de Quimica 70.848. disclosed a synthesis of four related benzodiazepines via solid phase parallel synthesis. Recently, Professor Ellmann of the University of California at Berkeley has disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514 and in numerous publications, which will be found in the Information Disclosure Sheet to be submitted in support of this application. Another relevant disclosure of parallel synthesis of small molecules may be found in U.S. Pat. No. 5,324,483. This patent discloses the parallel synthesis of between 4 and 40 compounds in each of sixteen different scaffolds.

Parallel, or combinatorial, synthesis has as its primary objective the generation of a library of diverse molecules which all share a common feature, referred to throughout this application as a scaffold. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules which explores a large percentage of the targeted space, the odds of developing a highly efficacious lead compound increase dramatically.

Parallel synthesis is generally conducted on a solid phase support normally on a polymeric resin. The scaffold, or other suitable intermediate is cleavably tethered to the resin by a chemical linker. Reactions are carried out to modify the scaffold while tethered to the solid support. Variations in reagents and/or reaction conditions produce the structural diversity which is the hallmark of each library.

As known in the art, parallel synthesis schemes are usually carried out in 96 well microtiter plates. The number of compounds desired to be produced will normally depend upon the range of space to be explored, usually from about 200 or 300 compounds up to more than 100,000. Theoretically, the total number of compounds which could be produced for a given library is limited only by the number of reagents available and the number of variable positions on the scaffold.

The greatest advantage of parallel synthesis is its adaptability to automation procedures. Once the actual reactions have been validated and confirmed, an entire library of compounds can usually be produced in less than a week. Considering that a typical research chemist manually synthesizes about 10–15 compounds per month, the speed and cost advantages of parallel synthesis are borne out.

The main disadvantage of parallel synthesis is purity, or more specifically, lack of purity. Since the same reaction conditions are used for all 96 compounds (assuming one compound per well), yields and purity may fluctuate greatly across the plate. This can cause false positive or negative results and may skew the overall data generated by the library. This disadvantage is lessened by utilizing proven and highly reliable methods of synthesis for the functionalized scaffolds to be produced.

After initially synthesizing and cataloging the library, the compounds are screened for potential biological activity. Active compounds are identified for secondary and tertiary screening, until a promising lead compound is identified for optimization and further work. Inactive compounds are held for future use against other potential targets.

Scaffolds are chosen for inclusion into a library based upon several factors such as size, known medicinal properties, known biological activity and pharmacaphoric properties, as well as ease of synthesis and the achievement of consistent yields and purity throughout the library. The functional groups used to modify the scaffold and product the sought-for molecular diversity are selected in much the same fashion.

SUMMARY OF THE INVENTION

This invention relates to processes for combinatorially producing a library of diverse compounds.

This general reaction scheme can be employed with any suitable scaffold, but the preferred scaffold is azetidinone. For purposes of this invention, the solid-phase combinatorial process is disclosed as useful in making compounds of the following general formula:

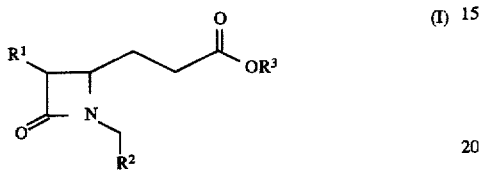

(I)

wherein $R^1$ and $R^2$ are each individually an amino acid residue mixture or a peptide mixture having two or more linked amino acids and $R^3$ is hydrogen or $C_1$-$C_6$ alkyl.

This invention also relates to a novel process for making the intermediate compounds of this invention, as well as a library of peptide analogs thereof. The compounds formed are pharmaceutically useful as confirmed by their biological activity in the Human Vasopressin (V1a) Receptor Binding Assay.

DETAILED DESCRIPTION OF THE INVENTION

The detailed description of the invention which follows is not intended to be exhaustive or to limit the invention to the precise details disclosed. It has been chosen and described to best explain the details of the invention to others skilled in the art.

This invention provides for methods of serially or sequentially producing compounds which make up a chemical library. All of the compounds in the library have a common backbone, referred to as the scaffold, and diverse functional groups attached to the scaffold. The functional groups are selected to allow the creation of a chemically diverse library which maximizes the exploration of molecular spatial properties. Such maximization increases the odds of creating compounds which will be biologically active against selected targets.

Scheme I below illustrates the preparation of the scaffold azetidinone molecule:

DEFINITIONS

"C1–C6 alkyl" refers to a straight or branched hydrocarbon chain of from one to six carbon atoms. Examples of C1–C6 alkyl include methyl, ethyl, propyl, butyl, pentyl and hexyl, as well as isopropyl, isobutyl, sec-butyl, t-butyl and other isomers.

"Protected amino acid" refers to an amino acid which includes an amino protecting group bonded to the nitrogen atom to prevent reaction. Examples of suitable amino protecting groups are 9-fluorenylmethoxycarbonyl (Fmoc), benzoxycarbonyl (BOC) and other similar carbamate forming moieties.

"Activated ester forming group" refers to a moiety attached to the terminal end of a carboxylic acid group in place of hydrogen, which moiety allows for selective peptide formulation when reacted with an amino acid. An example of an activated ester forming group is pentafluorophenyl (pfp).

SCHEME I

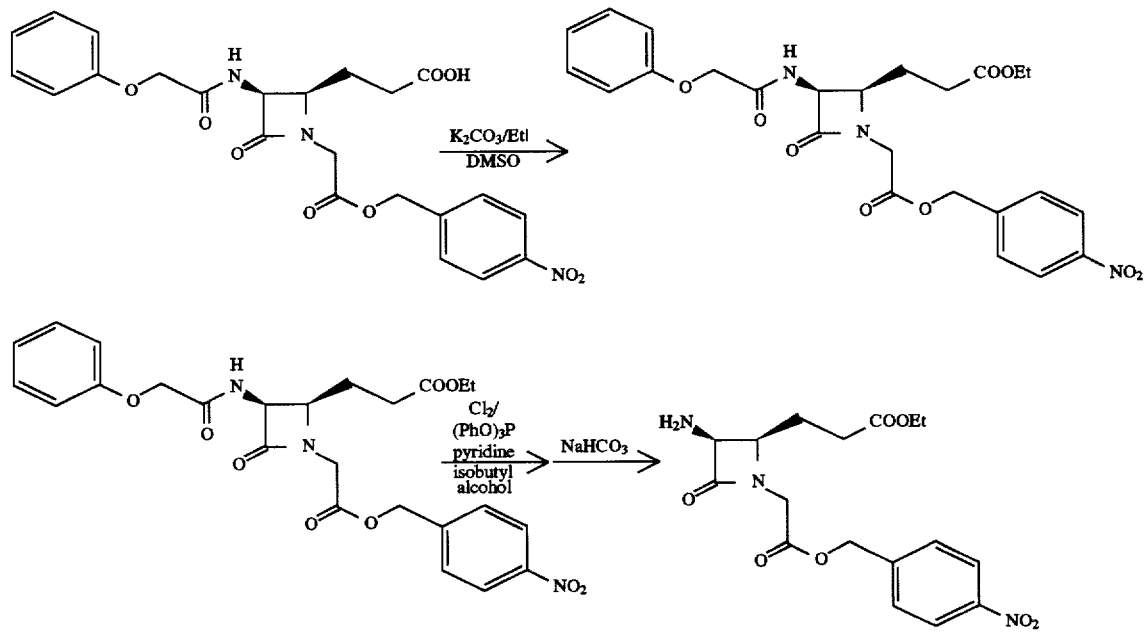

-continued
SCHEME I

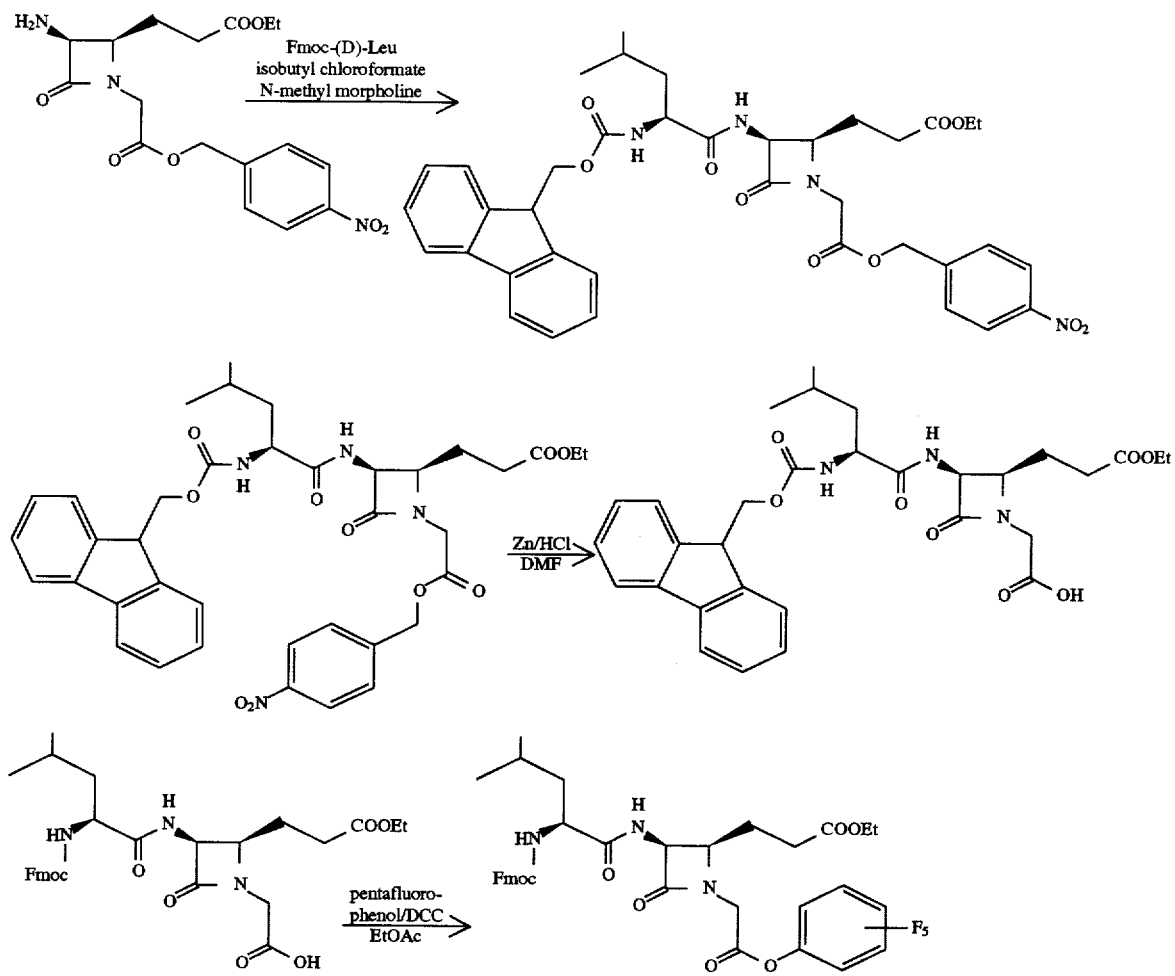

EXAMPLE 1

ESTERIFICATION

Into a 1 liter round bottomed flask was charged 3.8 g, 0.0275 mole of $K_2CO_3$ (anhydrous powder) and 200 mL of fresh, dry DMSO. This mixture was stirred under nitrogen and heated slightly (to 35°–40°) for about 20 minutes and then cooled back to room temperature. The starting propionic acid (23.85 g, 0.0491 mole) was added in one portion to the carbonate slurry which then began to form an incomplete solution. After 30 minutes, ethyl iodide (8.38 g., 4.3 mL, 0.0537 mole) was added in one portion and the reaction stirred at room temperature for 3 hours. An aliquot was worked up with water and ethyl acetate, the ethyl acetate layer was separated and reduced in volume to an oil, the oil reconstituted with acetonitrile and injected into an analytical HPLC (isocratic, 1:1 $CH_3CN/H_2O$, UV detector set at 254 nm). The tracing revealed a 90% conversion. An additional 1 mL of ethyl iodide was added to the reaction and the mixture was stirred at room temperature over night. HPLC analysis revealed a complete reaction in the morning. The reaction was quenched with cold water which caused some crystallization of product. The mixture was extracted with several portions of ethyl acetate. The combined extracts were washed with several portions of water to remove DMSO, dried with $MgSO_4$, filtered, and evaporated in vacuo to yield a crystalline product weighing 25 g. The structure was confirmed by comparative NMR analysis between the starting acid and the product. NMR ($CDCl_3$): TMS standard at 0.00 ppm, [3H: triplet, 1.2 ppm], [1H: multiplet, 1.7 ppm], [1H: multiplet, 1.95 ppm], [2H: double triplet, 2.22 ppm], [2H: doublet of doublets centered at 4.15 ppm, (3.95 ppm & 4.30 ppm)], [1H: multiplet, 4.05 ppm], [2H: quartet, 4.10 ppm], [1H: singlet, 4.55 ppm], [2H: singlet, 5.27 ppm], [1H: doublet of doublets centered at 5.38, (5.37 ppm & 5.39 ppm)], [2H: 6.92 ppm], [1H: triplet, 7.05 ppm], [3H: multiplet composed of a triplet and doublet, 7.30 ppm], [4H: doublet of doublets centered 7.89 ppm, (7.54 ppm & 8.25 ppm)].

EXAMPLE 2

SIDECHAIN CLEAVAGE

A three-fold excess of the chlorine/phosphite reagent solution was prepared. Into a 1 Liter, 4 neck, round bottom flask flushed with nitrogen was charged 500 mL dichloromethane and 1–2 drops dry pyridine. The flask was equipped with a magnetic stirring bar, –100° thermometer, a pressure equalizing addition funnel with nitrogen inlet, calcium chloride drying tube, chlorine inlet tube positioned just above the surface of the solution, all of this resting in a cooling bath. This solution was chilled to –40° with conservative use of dry ice into acetone and into the addition funnel was syringed, under nitrogen, 60.5 g, 51 mL triphenyl phosphite (3×0.065 mole). Chlorine gas was slowly blown into the flask over the surface of the liquid while a few mL of the phosphite was added. A slight exotherm was observed as well as the solution changing to a light yellow color. The chlorine addition was stopped and enough phosphite was added to dissipate the color back to colorless. After the temperature dropped back to near −40°, more phosphite and chlorine were added to repeat the above process and return the temperature to −40°. This adding, stopping, equilibrating, process was continued for the next 20–40 minutes until the phosphite was consumed and no yellow color was evident. A starch / KI test was performed on the solution determine the presence of active oxidants. No purple color was exhibited which indicated the solution was ready to use. If active oxidants were indicated by a purple color, additional phosphite could be added a few drops or mL at a time until no color appeared on the test paper. This solution must be kept cold (at least −20°) until use. One third of the total volume should contain approximately 1.3 equivalents (0.065 mole) of the chlorine / phosphite reagent solution which is what is needed for the following transformation.

A 500 mL, 3 neck round bottom flask was equipped with a magnetic stirring bar, −100° thermometer, calcium chloride drying tube, and a nitrogen inlet and positioned in a cooling bath. The flask was flushed with nitrogen and charged with 187 mL of the above chlorine / phosphite reagent solution. The contents of the flask were kept cold (below −20°) by the conservative addition of dry ice to acetone contained in the cooling bath. The diester azetidinone (25.65 g, 0.050 mole) was dissolved in 50 mL dichloromethane and added to the chlorine-complex reagent solution. Pyridine (5.37 g, 5.5 mL, 0.068 mole) was added to the reaction mixture which caused a slight exotherm. The reaction was stirred and allowed to warm slowly from −15° to 0° over the course of 90–110 minutes. Isobutanol (9 equiv., 33.3 g, 41.5 mL, 0.450 mole) was added to the reaction and the cooling bath was removed, allowing the temperature to increase further to 20°–25° over the next 2 hours. The reaction was quenched with ethyl acetate and ether to a slightly cloudy state and then evaporated to a gummy mass. Ether was added again and the mixture was triturated. After decanting the ether away, the process was repeated with several fresh portions of ether. This process removes most of the phosphate by-product. Water was added to dissolve the stiff, taffy-like material. Sodium bicarbonate was added to the aqueous solution to form the free base which was extracted with several portions of dichloromethane. The combined organic phase was back-washed with brine, dried with anhydrous sodium sulfate, filtered and evaporated to an oil (16.5 g) which carried the odor of pyridine. Extended evacuation reduced the pyridine odor to barely detectable levels if at all. The material was stored frozen due to its instability while characterization was completed. The structure was confirmed by NMR, and mass. spec. M=379. NMR (CDCl$_3$): TMS as standard: 0.0 ppm, [3H: triplet, 1.26 ppm], [2H: multiplet, 1.96 ppm], [2H: broad singlet, 2.1 ppm], [1H: multiplet, 2.35 ppm], [1H: multiplet, 2.48 ppm], [1H: multiplet, 3.85 ppm], [2H: doublet of doublets centered at 4.09 ppm, (3.90 ppm & 4.28 ppm)], [1H: broad multiplet, 4.42 ppm], [2H: singlet, 5.25 ppm], [ 4H: doublet of doublets centered at 7.90 ppm, (7.55 ppm & 8.25 ppm)]. C17 H21 N3 O7, mw=379.37, theory: C=53.82, H=5.58, N=11.08; found C=53.02, H=5.48, N=10.88.

EXAMPLE 3

MIXED ANHYDRIDE ACYLATION

A solution of Fmoc-(D)-leucine, 3.5 g, 10 millimole, in 20 mL dry DMF was prepared under nitrogen at room temperature. Once the solution formed, it was chilled to −15° and to it was added N-methyl morpholine, 1.01 g, 1.1 mL, 10 millimole, and after a 2 minute wait, isobutyl chloroformate, 1.36 g, 1.30 mL, 10 millimole, was added. This reaction mixture was stirred at −15° for 5 minutes and then added to a cold (−15°) solution of the 3-amino azetidinone, 3.8 g, 10 millimole, in 20 mL DMF. A drop of the reaction was tested with wet pH paper to check for the needed slight basic conditions and then stirred over night and allowed to warm to room temperature. After determining the reaction was still slightly basic, it was slowly quenched with saturated sodium bicarbonate solution (slight foaming), and evaporated to a thick residue. Ethyl acetate and water were added and the layers were separated. The aqueous layer was extracted 3×100 mL with ethyl acetate. The organic phases were combined and washed with water, 10×50 mL, to remove as much residual DMF as possible. After drying with Na$_2$SO$_4$, filtering, and evaporating the solution, a fluffy, off-white, crystalline solid (5.4 g) was obtained. The structure was confirmed by NMR, mass. spec. and elemental analysis. NMR (CDCl$_3$): TMS as standard at 0.0 ppm, [6H: broad doublet, 0.94 ppm], [3H: triplet, 1.21 ppm], [6H: broad multiplet, 1.60 ppm], [1H: multiplet, 1.93 ppm], [2H: multiplet, 2.22 ppm], [2H: doublet of doublets centered at 4.10 ppm, (3.93 ppm & 4.27 ppm)], [1H: multiplet, 3.97 ppm], [2H: multiplet, 4.08 ppm], [2H: multiplet, 4.25 ppm], [1H: multiplet, 4.45 ppm], [1H: doublet, 5.12 ppm], [2H: singlet, 5.25 ppm], [1H: multiplet, 5.26 ppm], [2H; triplet, 7.31 ppm], [2H: triplet, 7.40 ppm], [2H: doublet, 7.51 ppm], [2H: doublet, 7.59 ppm], [2H: doublet, 7.77 ppm], [2H: doublet, 8.22 ppm]. Mass spec., M=714. Elemental analysis: $C_{38}$ $H_{42}$ $N_4$ $O_{10}$, mw=714.78, theory C=63.86, H=5.92, N=7.84; found C=63.86, H=5.77, N=7.60.

EXAMPLE 4

REDUCTIVE ESTER HYDROLYSIS

Into a 500 mL single neck spherical flask was charged 160 mL DMF and 5.0 g (7 millimole) of the Fmoc-(D)-leucyl azetidinone pNB ester. After dissolution, the contents of the flask were chilled to −5° and treated with 16 mL (56 millimole) 5N HCl solution. When the solution had cooled again to −5°, zinc dust, 2.73 g, 42 millimole, was added in 3 portions over 3 minutes. A slight exotherm ensued taking the temperature to 3°. The reaction was stirred for 90 minutes at 0° and then the cooling bath was removed to allow the reaction to come to room temperature over the next 90 minutes. The unreacted zinc dust was removed by filtration and washed with DMF. The filtrate and wash were evaporated to a thick yellow syrup. Upon adding 0.5N HCl to this material, a heavy mass of insoluble, tacky yellow material precipitated. Water and ethyl acetate were added and the mixture was triturated and then poured over a filter to remove the yellow, gummy solid. The layers were separated and the aqueous was extracted with ethyl acetate, 6×75 mL. The combined extracts were subsequently washed with 3, 75 ML portions of water to remove most of the residual DMF. After filtering, the wet solution was evaporated to a syrup (an NMR spectrum revealed a substantial amount of DMF present). Water and ethyl acetate were added and the mixture was re-evaporated followed by water and toluene additions and azeotropic evaporation again. This produced a light yellow crystalline material, which by NMR showed only a small % of DMF remaining. The light yellow solid was re-dissolved in ethyl acetate, treated with decolorizing charcoal and Na$_2$SO$_4$, filtered, and evaporated to yield 3.4 g of off-white solid. The structure was confirmed by 300 mHz NMR, mass. spec. and by elemental analysis. NMR (DMSO $d_6$), TMS as standard at 0.0 ppm, [6H: triplet, (overlapping doublet), 0.84 ppm], [3H: triplet,1.16 ppm], [1H: multiplet, 1.30 ppm], [3H: multiplet,1.55 ppm], [1H: multiplet, 1.92 ppm], [2H: multiplet, 2.15 ppm], [1H: multiplet, 3.77 ppm], [2H: doublet of doublets centered at 4.07 ppm, (3.89 ppm & 4.22 ppm], [2H: quartet, 4.01 ppm], [1H: multiplet, 4.19 ppm], [2H: multiplet, 4.22 ppm], [1H: singlet, 4.23 ppm], [1H: multiplet, 5.05 ppm], [2H: multiplet, 7.34 ppm], [2H: triplet, 7.42 ppm], [1H: doublet, 7.56 ppm], [2H: doublet, 7.75 ppm], [2H: doublet, 7.91 ppm], [1H: doublet, 8.97 ppm], [1H: broad singlet, 12.92 ppm]. Mass spec: M=579. Elemental analysis for $C_{31}$ $H_{37}N_3$ $O_8$, mw=579.66: theory, C=64.24, H=6.43, N=7.25; found, C=64.47, H=6.50, N=7.22.

EXAMPLE 5

ACTIVE ESTER PREPARATION

Into a 500 mL, 3 neck round bottom flask equipped with a magnetic stirring bar, calcium chloride drying tube, thermometer, addition funnel with nitrogen inlet, and resting in a cooling bath, was charged, under a blanket of nitrogen, 1.06 g, 5.2 millimole, dicyclohexylcarbodiimide (DCC) in 25 mL fresh ethyl acetate. This was chilled to 0° and to it was added, under nitrogen, a chilled solution of 1.00 g, 5.4 millimole pentafluorophenol in 15 mL ethyl acetate. An additional 10 mL ethyl acetate was used to rinse in the phenol remnants. A solution of the Fmoc protected azetidinone carboxylic acid in 250 mL ethyl acetate, which had previously been prepared, was poured into the addition funnel. After the DCC and pentafluorophenol solution stirred in the cold for 5 minutes, the Fmoc protected azetidinone solution was added over approximately 15 minutes and at such a rate that the reaction temperature was kept below 5°. After the addition was complete, the reaction solution was stirred at 0° for 5 hours. The precipitated DCU was collected on a filter and washed with ethyl acetate. The filtrate and wash were combined and evaporated to a crystalline solid that retained a slight phenolic odor. The yield was quantitative and the structure was confirmed by NMR and by mass. spec. NMR ($CDCl_3$), TMS as standard at 0.0 ppm, [6H: broad doublet, 0.90 ppm], [3H: triplet, 1.21 ppm], [1H: multiplet, 1.30 ppm], [1H: multiplet, 1.56 ppm], [2H: multiplet, 1.65 ppm], [1H: multiplet, 1.95 ppm], [2H: multiplet, 2.27 ppm], [1H: multiplet, 4.01 ppm], [2H: quartet, 2.10 ppm], [2H: multiplet, 4.22 ppm], [2H: doublet of doublets centered at 4.39 ppm, (4.25 ppm & 4.54 ppm)], [2H: multiplet 4.42 ppm], [1H: doublet, 5.23 ppm], [1H: multiplet, 5.35 ppm], [3H: doublet and triplet, 7.30 ppm], [2H: triplet, 7.38 ppm], [2H: doublet, 7.59 ppm], [2H: doublet, 7.77 ppm]. Mass spec shows molecular ion at 746 (calculated mw=745).

The scaffold molecule is useful as an intermediate for the preparation of a combinatorial library of compounds. In this invention, substitution at the Ni and the C3 groups was selected and amino acids selected as the building blocks for substitution. This selection process was influenced by commercial availability of (D)-amino acids, as well as their ability to rapidly and combinatorially form peptide-like chains.

Library size was limited to ease in characterization and deconvulution after an assay hit is recoreded. Further, in the first library of 25 compounds, one of the three amino acids (added stepwise in mixture fashion as described below) to further ease the deconvolution problem.

In the second library, seven different amino acids were used to prepare the 343 tripeptide azetidinone compounds as a mixture. Since the molecular interactions in the use of amino acids to form peptides are very similar, the method of this invention may also employ any number of amino acids in the mixture. Mixtures will preferably include each of the twenty naturally occurring amino acids, which would yield a library of 8000 tripeptide azetidinone compounds.

The combinatorial process, as exemplified in the Schemes and Examples to follow, involves the tacking on of amino acids at selected points of the azetidinone scaffold. The formula (II) scaffold

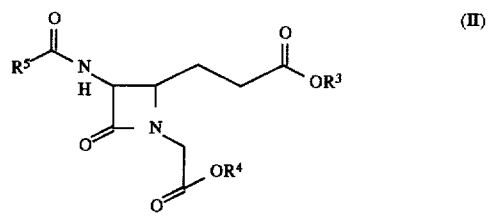

wherein $R^3$ is $C_1$–$C_6$ alkyl;

$R^4$ is hydrogen or an activated ester forming group; and $R^5$ is a protected amino acid;

is contacted with a mixture of protected amino acids which attach to the terminal end of the Ni moiety to form the formula (III) intermediates:

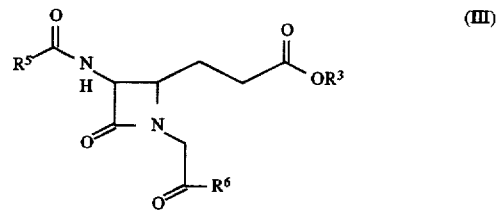

wherein $R^6$ is said mixture of said plurality of protected amino acids.

The $R^6$ moiety is then deprotected in a common fashion, usually with piperidine, and the mixture of amino acids is again introduced to form the $R^2$ dipeptide moiety.

To produce a tripeptide the $R^6$ moiety is again deprotected and the amino acid mixture reintroduced. The terminal $R^6$ amino acid is deprotected to leave a terminal amine group. To produce longer chains of peptide mixtures, the above process is repeated once for each mixture of amino acids added to the chain.

The amino acid mixtures are preferably formed on a solid support, more preferably on synthetic polymeric resin beads, most preferably on Fmoc/Knorr resin which is well known in the art. Fmoc/Knorr resin is commonly used for combinatorial peptide synthesis because of its desirable properties of easy linkage and clean cleavage under fairly normal conditions. The exact procedures for deprotection, amino acid linkage and amino acid cleavage from Fmoc/Knorr resin are explained below.

It should be noted that in each of the Schemes, the stereochemistry shown is the preferred stereochemistry and is not limitative of the invention. Also, to aid in identification of the compounds in the 343 number library, the first amino acid in the chain is known. Seven different known compounds are subjected to the two-part addition to form seven series of 49 tripeptides as explained in Scheme III.

Schemes II-IV and Examples below illustrate the preparation of a singular tripeptide substituted azetidinone, a 25 member peptide library and a 343 member library utilizing the process of this invention.

The Fmoc/Knorr resin was purchased from Advanced ChemTech and had an activity of 0.5 meq/gram.

SCHEME II

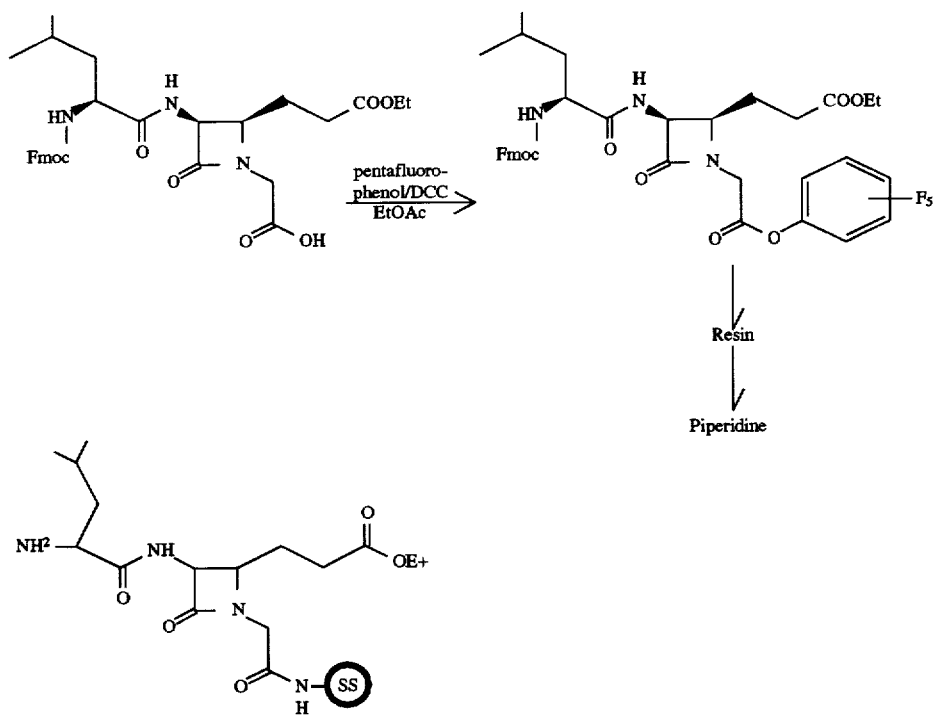

EXAMPLE 6
A singular azetidinone based tripeptide

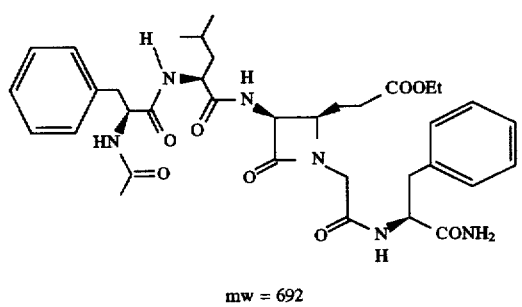

mw = 692 was prepared via the proposed route envisioned for the more extensive azetidinone based combinatorial mixtures. The Fmoc protected D-phenyl alanine used in the sequence was purchased from Advanced ChemTech and further activated as the pentafluorophenyl ester (pfp) in our laboratory. The azetidinone was functionalized and protected in our laboratory from a commercial process intermediate and also used as the pentafluorophenyl ester. The pfp esters were prepared in the way described by Kovacs, et. al. The solvents: dimethyl formamide (DMF), dichloromethane (DCM), methanol (MeOH), were Aldrich "Sure-Seal" anhydrous solvents. The piperidine and anhydrous trifluoroacetic acid (TFA) were also purchased from Aldrich. The mechanical apparatus and the vessels were DuPont "RaMPS" items. The cleavage vessel used was one available from Bio-Rad and has a capacity of ~5 mL. The capped vessel has an integral polypropylene filter and a Leur tip with break-away seal.

The azetidinone structure is displayed below.

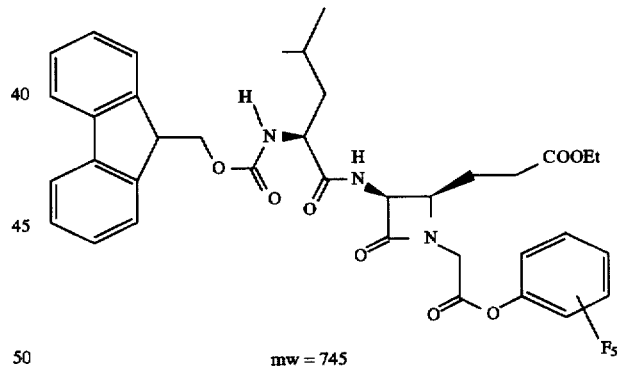

mw = 745

A single RaMPS vessel was charged with 200 mg Fmoc/Knorr resin. The resin was treated with DMF for swelling purposes and rocked for 15 minutes. The liquid was drained and the process was repeated 3 times more. The resin was treated with a 25% solution of piperidine in DMF and rocked for 10 minutes. The liquid was drained and the resin washed several times with DMF, MeOH and again with DMF so that no odor of piperidine remained. A ninhydrin test on a few of the resin beads displayed the characteristic deep blue color indicating ample free amine. The main resin body was treated with 1 mL DMF to soak. Fmoc-D-phenylalanine pfp ester (mw=553) was dispensed, 111 mg each, into 4, 20 mL vials w/ screw caps. The contents of one of the vials was dissolved with 1 mL DMF and added to the RaMPS vessel containing the resin. DMF, 1 mL, was used as a rinse for the vial and this was added to the reaction vessel. The reaction vessel was then rocked for 2 hours and followed by a ninhydrin test which indicated by color that substantial coupling had taken place. The reaction was rocked for an additional hour and the liquid was drained. The resin was washed once with DMF and re-soaked with 1 mL DMF. The contents of a second vial of the Fmoc D-phenylalanine pfp ester was dissolved in 1 mL DMF, added to the reaction vessel and followed by the rinse from the vial. The reaction was rocked for 2 hours and tested by the ninhydrin method which indicated that complete coupling had occurred. The liquid was drained and the resin was washed several times with DMF, MeOH, and DMF with a final 1 mL DMF added for soaking. The Fmoc protecting group was removed as before with the piperidine/DMF treatment and followed by the ninhydrin test to reveal free amine. The azetidinone was dispensed, 150 mg each, into 2, 20 mL glass vials w/ screw caps. The contents of one of these azetidinone vials was dissolved with 1 mL DMF and added to the reaction vessel followed by the 1 mL rinse. The reaction vessel was rocked for 2 hours and a sample of the beads was washed and subjected to the ninhydrin test. The color indicated incomplete coupling and the rocking was continued an additional hour. The liquid was drained, the resin was washed with DMF and the second charge of the azetidinone was added and the reaction was rocked for 2 hours. A ninhydrin test indicated the coupling was complete. The resin was washed well with DMF, MeOH, and DMF. The above general procedure then was followed again to remove the Fmoc protection and to couple the last 2 charges of the Fmoc-D-phenylalanine. After washing well with DMF, DCM,-MeOH, DMF the resin bound material was Fmoc deprotected and treated with 1:1 DMF acetic anhydride to cap the N terminus. After rocking 1 hour, ninhydrin indicated the material was completely acetylated. This material was washed well with DMF, DCM, MeOH and vacuum dried @40° for 4 hours. The material was transferred to a Bio-Rad vessel and treated with ice cold anhydrous TFA to cleave the product from the resin. After capping the vessel and shaking vigorously, the vessel was placed in ice water for 30 minutes. The bottom seal was removed and the rose colored liquid was drained into a tared spherical flask. The spent resin was rinsed with 2 mL cold TFA and this rinse was added to the original filtrate. These combined liquors were evaporated with no external heating to a residue. The residue was treated with anhydrous ether and evaporated to further remove residual TFA. The resulting residue was treated again with anhydrous ether to form a slurry. After allowing this to set for -5 minutes, the liquor was decanted and the process was repeated 2 times more resulting in some mechanical losses. The remaining residue was evaporated to dryness. No odor of TFA was evident. While all of these manipulations were going on, the spent resin was re-treated with cold TFA and allowed to set in ice-water for another 30 minutes so as to possibly provide a second crop. A first crop of 26.2 mg as well as a second crop of 20 mg were collected. Both crops displayed a mass of 692 in Ion-spray mass spec. (Cal. MW=692)

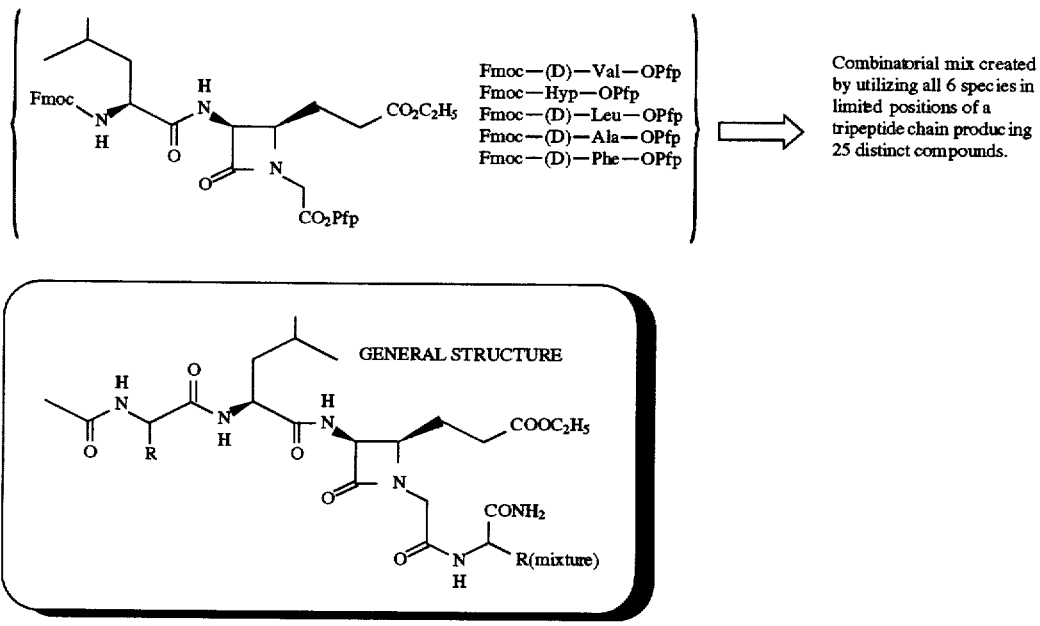

The (D)-Leu-azetidinone acetic acid is defined as a single amino acid and has the symbol

SPECIFIC MIXTURES

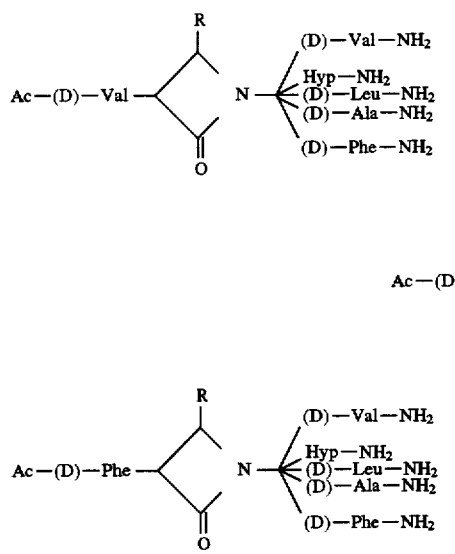

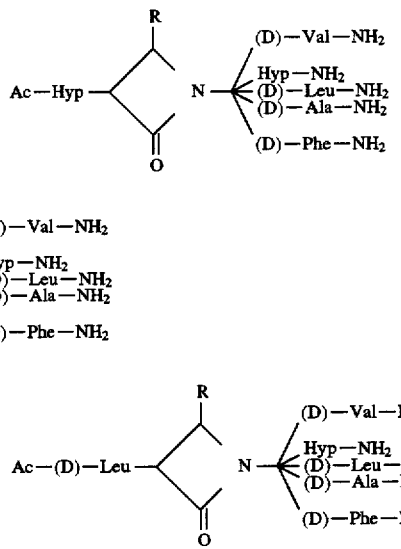

EXAMPLE 7

The 5×1×5 azetidinone based mixed combinatorial peptide library was prepared in the following manner. All Fmoc protected amino acids used in the sequence were purchased from Advanced ChemTech and further activated as the pentafluorophenyl esters (pfp) in our laboratory. The azetidinone was functionalized and protected in our laboratory from a commercial process intermediate and also used as the pentafluorophenyl ester. The pfp esters were prepared in the way described by Kovacs, Kisfaludy and Ceprini at 89 J.Amer.Chem.Soc. 183(1967). The solvents: dimethyl formamide (DMF), dichloromethane (DCM), methanol (MeOH), were Aldrich "Sure-Seal" anhydrous solvents. The piperidine and anhydrous trifluoroacetic acid (TFA) were also purchased from Aldrich. The mechanical apparatus and the vessels were DuPont "RaMPS" items. The ninhydrin test solutions were also from DuPont. The cleavage vessel used was one available from Bio-Rad and has a capacity of ~5 mL. The capped vessel has an integral polypropylene filter and a Leur tip with break-away seal. The Fmoc Knorr resin was purchased from Advanced ChemTech and had an activity of 0.5 meq/gram. 200 mg of the Knorr resin was used in each RaMPS vessel.

| The Fmoc amino acids used were: | mw | weight used |
|---|---|---|
| A, D-valine pfp ester | 505 | 202 mg |
| B, trans-L-Hydroxyproline pfp ester | 519 | 208 mg |
| C, D-leucine pfp ester | 519 | 208 mg |
| D, D-alanine pfp ester | 477 | 191 mg |
| E, D-phenyl alanine pfp ester | 553 | 222 mg |

The total amount of the Fmoc amino acids was 0.400 milliMole. The total amount of the Fmoc azetidinone compound was 5×0.400=2.0 milliMole, or 1.50 g. This material was used exclusively in the second coupling. Each of the above 5 Fmoc amino acids were divided equally by 4 and each portion placed in a separate, appropriately labeled 20 mL glass vial w/ screw cap. The Fmoc azetidinone was divided by 2 and placed in 2 vials as described above.

Each of 5 RaMPS vessel was charged with 200 mg of Knorr resin and placed in the RaMPS rocker. The resin was swelled with DMF for 10 minutes and drained. This process was repeated twice more and then the resin was treated with 1.0 mL of 25% solution of piperidine in DMF. The vessels were capped and rocked for 10 minutes and then drained. The material in the vessels was washed 4 times with DMF, 3 times with MeOH and 3 times with DMF again. No odor of piperidine was detected. The resin masses were swelled with DMF. A few beads of the resin from each vessel were sucked out of the vessels and placed in glass test tubes and treated with the ninhydrin solutions and heated to indicate an abundance of free amine. The contents of one each of the vials of the 5 different Fmoc amino acid pfp esters were treated with 1.0 mL DMF (followed by 1.0 mL DMF as a rinse) to form a solution and then discharged, one into each of the 5 resin containing vessels to being the coupling process. Thus, Fmoc D-valine was charged into vessel "A", Fmoc Hyp was transferred to vessel "B", etc. The vessels were capped and rocked for 2 hours. A small sample of the beads from each vessel was sucked out and placed into a clean glass test tube. (The vessels were recapped and the rocking was continued during the ninhydrin test.) The beads were washed by decantation twice with DMF and twice with MeOH. Treatment with the ninhydrin solutions and subsequent heating indicated the resin in most of the vessels was almost completely coupled. The rocking was continued another hour and then the liquids were drained from each vessel. 1.0 mL DMF was used to rinse through the beads and the second charge of the same pfp ester was added to the appropriate resin containing vessel. Thus, the contents of the second vial of Fmoc D-valine were dissolved in 1.0 mL DMF and added (followed by a 1.0 mL DMF rinse) to same resin containing vessel that received the first charge of Fmoc D-valine. This procedure was followed for all the Fmoc amino acid pfp esters. The rocking was continued for three hours and the ninhydrin test was run again this time showing that all were completely coupled. The liquids were drained from the resin vessels and a series of rinses with (3×) DMF (3×) MeOH was done. The contents of each of the resin vessels were then carefully washed out of the vessels with MeOH into a common beaker and all were intimately mixed. The beads were slurried and transferred by pipette back into the same RaMPS vessels and drained. The amount per vessel was adjusted by transfer pipette to as even a volume (visually) as possible. The beads were soaked and swelled with 1.0 mL DMF for 10 minutes and drained. The process was repeated 2 times more. The piperidine/DMF treatment was repeated as above and the resin was rinsed and tested with ninhydrin reagent to show free amine. One of the vials containing the azetidinone was treated with 5 mL DMF and the resulting solution was added equally to the 5 resin containing vessels. The vial was rinsed with 5 mL DMF and this rinse was added evenly to the 5 reaction vessels. The rocking was started and continued for 2 hours and then a few beads from each vessel were pipetted out and placed in glass test tubes. After washing, the beads were subjected to the ninhydrin test which showed most couplings were proceeding well. The reactions were continued for another hour and then the vessels were drained of their liquid contents. After washing with DMF, the second charge of the Fmoc azetidinone was added to the 5 RaMPS vessels and the rocking was started. After 3 hours, ninhydrin tests showed all the couplings had proceeded well. The resin in each vessel was washed 3 times with DMF. Note: No mixing has taken place! The resin was treated with piperidine/DMF solution and rocked for 10 minutes and then drained. After washing well with DMF (no piperidine odor remained), a small sampling of beads from each vessel was subjected to a ninhydrin test which revealed abundant free amine. The resin in each vessel was soaked with DMF and treated with the final round of Fmoc amino acid esters. After rocking 2.5 hours, a ninhydrin test was done on small samples from each vessel which showed incomplete coupling. The vessels were drained of their liquid and the resin rinsed with DMF. The final charge of Fmoc amino acid pfp esters was added to the appropriate vessels and the rocking continued for 3 hours. Ninhydrin tests showed complete coupling. The resins were rinsed several times and then treated with the piperidine solution in the usual manner. After ninhydrin displayed potent amine presence, the resins were rinsed with copious amounts of DMF to remove all residual piperidine. DMF was added to each vessel followed by 1 mL of acetic anhydride. After a 1 hour coupling time, ninhydrin indicated a complete coupling. The resins were washed well with DMF, MeOH, and DCM. The vessels containing their resins were placed in a vacuum oven and dried at 40° for 4 hours. Each separate resin was transferred to labeled (A, B, . . . etc.) Bio-Rad reaction vessels that contain a polypropylene filter and a break away seal on the drip tip under the filter. Into this vessel was pipetted 2.0 mL ice cold anhydrous TFA, the vessel was capped on the top, shaken vigorously and placed in ice/water for 30 minutes. This is the cleavage process that removes the peptide from the resin.

The bottom seals were broken away and the rose colored liquid was drained into tared spherical flasks. The spent resin was quickly rinsed with 2×1 mL TFA and the rinses were added to the original filtrate. The combined filtrates of a single reaction vessel were then evaporated without using any external heat to quicken the evaporation rate. Meanwhile, the spent resin was treated again with 2.0 mL TFA and the cold, 30 minute cleaving process was repeated to reap a second crop if possible. The residue from the evaporated original filtrates was treated with anhydrous ether and evaporated quickly and then slurried again with more ether. After setting for about 5 minutes, the ether was decanted and this process was repeated often with some mechanical losses of material. The residual ether was evaporated and the residue was checked (by odor) to determine if TFA was present. If the faintest odor was detected, the ether treatments were repeated. Afterwards, the labeled flasks were weighed and placed in the freezer @−20°. This process was repeated separately for each of the 5 reaction vessels. Thus, a combinatorial mixture of 5 tripeptides with N-acetyl D-valine at its N terminus and amide at its carboxyl terminus was prepared as "A". Another similar set of 5 tripeptides with N-acetyl hydroxyproline replacing the D-valine was prepared as "B". N-acetyl-D-leucine terminated the set known as "C", D-ala was the common terminus in "D", and D-phenylalanine was distinctive for "E". All 5 mixtures contained the azetidinone as the central peptide moiety and all of the 5 amino acids as amides at the carboxyl terminus. Ion spray mass spec, amino acid analyses, UV, IR, and titrations were performed on the mixtures.

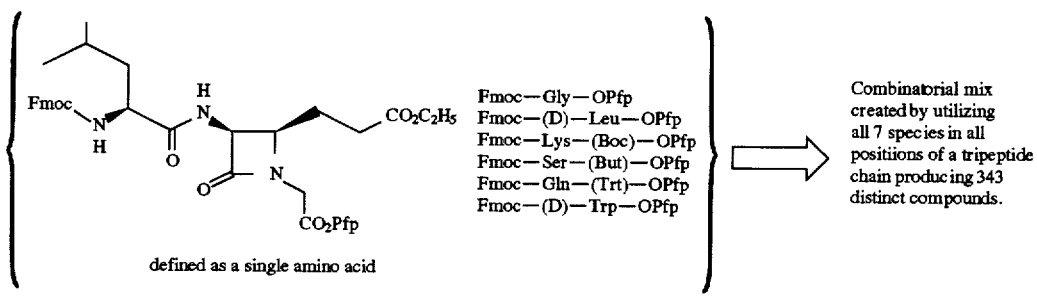

The (D)-Leu-azetidinone acetic acid is defined as a single amino acid ad is labeled as "azet".

The typical mixture could be pictured in the same manner as the glycine terminated mixture is diagramed below.

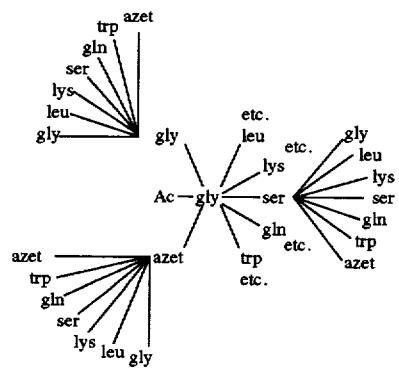

EXAMPLE 8

The 7×7×7 combinatorial mixture azetidinone based peptide library was prepared in the following manner. All Fmoc protected amino acids used in the sequence were purchased from Advanced ChemTech and further activated as the pentafluorophenyl esters (pfp) in our laboratory. The azetidinone was from a commercial process intermediate and was functionalized and Fmoc protected in our laboratory. It also was used as the pentafluorophenyl ester. The pfp esters were prepared in the way described by Bodansky & Bodansky. The solvents: dimethyl formamide (DMF), dichloromethane (DCM), methanol (MeOH), were Aldrich "Sure-Seal" anhydrous solvents. The piperidine and anhydrous trifluoroacetic acid (TFA) were also purchased from Aldrich. The mechanical apparatus and the vessels were DuPont "RaMPS" items. The ninhydrin test solutions were also from DuPont. The Fmoc Knorr resin was purchased from Advanced ChemTech and had an activity of 0.5 meq/gram.

The Fmoc amino acids used were:

| | | |
|---|---|---|
| A, glycine pfp ester | 1.04 g | for vessel "A" |
| B, D-trp pfp ester | 1.35 g | for vessel "B" |
| C, L-Leu pfp ester | 1.16 g | for vessel "C" |
| D, L-Gln (Trt) pfp ester | 1.75 g | for vessel "D" |
| E, D-lys (Boc) pfp ester | 1.43 g | for vessel "E" |
| F, L-Ser (But) pfp ester | 1.24 g | for vessel "F" |
| G, azetidinone pfp ester | 1.67 g | for vessel "G" |

Each of the above materials was divided equally by 6 and each portion placed in a separate, appropriately labeled 20 mL glass vial w/ screw cap.

Each of 7 RaMPS vessel was charged with 250 mg of Knorr resin and placed in the RaMPS rocker. The resin was swelled with DMF for 10 minutes and drained. This process was repeated twice more and then the resin was treated with 1.0 mL of 25% solution of piperidine in DMF. The vessels were capped and rocked for 10 minutes and then drained. The material in the vessels was washed 4 times with DMF, 3 times with MeOH and 3 times with DMF again. No odor of piperidine was detected. The resin masses were swelled with DMF. A few beads of the resin from each vessel were sucked out of the vessels and placed in glass test tubes and treated with the ninhydrin solutions and heated to indicate an abundance of free amine. The contents of one each of the vials of the 7 different pfp esters were treated with 1.0 mL DMF (followed by 1.0 mL DMF as a rinse) to form a solution and then discharged, one into each of the 7 resin containing vessels to being the coupling process. Thus, Fmoc glycine was charged into vessel "A", Fmoc D-trp was transferred to vessel "B", etc. The vessels were capped and rocked for 2 hours. A sample of the beads from each vessel was sucked out and placed into a clean glass test tube. (The vessels were recapped and the rocking was continued during the ninhydrin test.) The beads were washed by decantation twice with DMF and twice with MeOH. Treatment with the ninhydrin solutions and subsequent heating indicated the resin in most of the vessels was almost completely coupled. The rocking was continued another hour and then the liquids were drained from each vessel. 1.0 mL DMF was used to rinse through the beads and the second charge of the same pfp ester was added to the appropriate resin containing vessel. Thus, the contents of the second vial of Fmoc glycine were dissolved in 1.0 mL DMF and added (followed by a 1.0 mL DMF rinse) to same resin containing vessel that received the first charge of Fmoc glycine. This procedure was followed for all the Fmoc amino acid pfp esters. The rocking was continued for three hours and the ninhydrin test was run again this time showing that all were completely coupled. The liquids were drained from the resin vessels and a series of rinses with (3×) DMF (3×) MeOH was done. The contents of each of the resin vessels were then carefully washed out of the vessels with MeOH into a common beaker and all were intimately mixed. The beads were slurried and transferred by pipette back into the same RaMPS vessels and drained. The amount per vessel was adjusted by transfer pipette to as even a volume (visually) as possible. The beads were soaked and swelled with 1.0 mL DMF for 10 minutes and drained. The process was repeated 2 times more. The piperidine/DMF treatment was repeated as above and the resin was rinsed and tested with ninhydrin reagent to show free amine. This next coupling phase was conducted exactly as the first round was using the same sequence, i.e., Fmoc glycine pfp in vessel "A", etc. After determining by ninhydrin testing (some three hours later) that all the couplings were nearly complete, the vessels were drained and the resin washed in the same fashion as before. The second charge of Fmoc amino acid pfp was dissolved in the DMF as described earlier and added to the appropriate resin/vessel. Rocking was done for 3 hours, ninhydrin indicated complete coupling and the resin was drained. After washing with solvents as described earlier, the resins were again mixed by flushing into a common beaker with MeOH. After visually re-dividing the resin slurry by pipette into the RaMPS vessels, the repeated soaking, swelling and flushing by DMF was done to ready the resin for the final coupling. Treatment with the piperidine solution to remove the Fmoc protection followed by the ninhydrin test allowed the double coupling technique to proceed. After this last coupling was completed and thoroughly washed, the resin was treated with the piperidine solution one last time. After thoroughly rinsing and checking with ninhydrin, the resin bound peptides were again swelled with DMF and treated with 2 mL acetic anhydride to cap the terminal amino function. This process was finished quickly and completely in less than 1 hour. The resin material was again drained and thoroughly rinsed with DMF, MeOH and DCM and finally vacuum dried at 40° for 4 hours. Each separate resin was transferred to labeled (A, B, . . . etc.) Bio-Rad reaction vessels that contain a polypropylene filter and a break away seal on the drip tip under the filter. Into this vessel was pipetted 2.0 mL ice cold anhydrous TFA, the vessel was capped on the top, shaken vigorously and placed in ice/water for 30 minutes. This is the cleavage process that removes the peptide from the resin as well as removing other protecting groups from the peptides. The bottom seals were broken away and the rose colored liquid was drained into tared spherical flasks. The spent resin was quickly rinsed with 2×1 mL TFA and the rinses were added to the original filtrate. The combined filtrates of a single reaction vessel were then evaporated without using any external heat to quicken the evaporation rate. Meanwhile, the spent resin was treated again with 2.0 mL TFA and the cold, 30 minute cleaving process was repeated to reap a second crop if possible. The residue from the evaporated original filtrates was treated with anhydrous ether and evaporated quickly and then slurried again with more ether. After setting for about 5 minutes, the ether was decanted and this process was repeated often with some mechanical losses of material. The residual ether was evaporated and the residue was checked (by odor) to determine if TFA was present. If the faintest odor was detected, the ether treatments were repeated. Afterwards, the labeled flasks were weighed and placed in the freezer @−20°. This process was repeated separately for each of the 7 reaction vessels.

Thus, a combinatorial mixture of 49 tripeptides with N-acetyl glycine at its N terminus and amide at its carboxyl terminus was prepared as "A". Another similar set of 49 tripeptides with D-tryptophan replacing the glycine was prepared as "B". N-acetyl-L-leucine terminated the set known as "C". L-glutamine was the common terminus in "D", D-lysine was distinctive for "E", L-serine for "F" and the azetidinone provided the marker for "G". The calculated molecular weights should range from a minimum of 230 in "A" to a maximum of 1076 in "G".

|  | average mw (calculated) |
|---|---|
| A1, 14 mg ... A2, 7 mg | 512 |
| B1, 12.9 mg | 640 |
| C1, 11.2 mg ... C2, 4.6 mg | 568 |
| D1, 13.2 mg ... D2, 21.2 mg | 583 |
| E1, 25.7 mg | 583 |
| F1, 23 mg | 542 |
| G1, 25 mg | 794 |

Due to the complexity of each of the mixtures, normal analytical methods were not pursued.

The compounds of the 343 member library were then assayed (as mixtures) for biological activity in the Vasopressin (Human V1a) Receptor Binding Assay. The protocol for this assay is as follows:

1. Harvest hV1a cells from 20 roller bottles, centrifuge at 2500 rpm for 10 minutes. Remove supernatant, and add 40 mls Tris buffer (50 mM, pH 7.4) to pellet. Homogenize pellet with a Tekmar tissumizer for 1 minute. Centrifuge at 40,000×g (18000 RPM) for 10 min. Pour off supernatant and resuspend pellet in 40 ml of Tris buffer using homogenizer as above. Repeat centrifugation. Suspend the final pellet in 80 ml of Tris buffer with homogenizer and freeze 4 ml aliquots at −80° C. For assay, aliquot is diluted to 25 μg/ml protein. Protein concentration determined by BCA assay (Pierce).

| ASSAY BUFFER | 50 mM HEPES pH 7.4 | 23.83 g/2L |
|---|---|---|
|  | 5 mM MgCl2 (6H2O) | 1.02 g/2L |
|  | 1 mM Dithiothreitol (DTT) | 308.4 mg/2L |
|  | Bacitracin (after buffer pH adjusted) | 80.0 mg/2L |

1 mg/100 ml Aprotinin (add fresh to amount of buffer needed for assay)

2. FILTERS: soak GF/B filters for 2 hours in 20 mg/100 ml BSA−0.4 g/100 ml PEI (polyethyleneimine-50%) in 50 mM Tris, pH 7.7.

3. 3H-VASOPRESSIN: 3HPMP-AVP (vasopressin antagonist), 56 Ci/mM in 1 mCi/ml ethanol. Add 1 ul to 20 ml of assay buffer for stock 3H solution 100 ul of this is used for each sample to give a final concentration of 0.2 pM (0.1 pmoles/0.5 ml of incubation).

4. Compounds are dissolved in DMSO and 5 ul added to each sample.

5. Standard: PMP-AVP, 1 mM in dilute acetic acid. Make serial dilutions in DMSO 100 times final concentration and add 5 ul to each tube. Final concentrations are:

| INCUBATION: add | 195 ul buffer |
|---|---|
|  | 200 ul homogenate |
|  | 5 ul sample in DMSO |
|  | 100 ul 3H-PMP-AVP |

6. Incubate one hour at room temperature.

7. Filter with cell harvester using 50 mM Tris, pH 7.7 wash buffer.

8. Put filter circles in scintillation vials, add 5 ml. Ready Protein Plus scintillation fluid and count.

As described above, the library was divided into seven groups of 49 compounds each, based on the known value of the first amino acid residue in the tripeptide chain. The B series of 49 azetidinone tripeptides had a structure of:

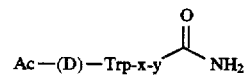

where X and Y are mixtures of amino acid residues from the seven amino acids used in Example 8.

This series of compounds had an $IC_{50}$ of 83 ug/ml, which computes to a molar $IC_{50}$ of approximately 2.6 uM for each compound on average. Since inhibition of V1a receptors in humans is associated directly with anti-hypertensive effects, these compounds, or mimics thereof are seen as potentially useful cardiovascular therapeutics.

We claim:

1. A process for combinatorial preparation of a library of azetidinone analogs each having the general formula:

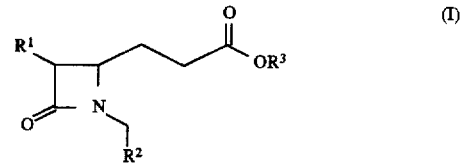

wherein $R^1$ and $R^2$ are each individually an amino acid residue or a peptide, said peptide having two or more linked amino acids, and $R^3$ is hydrogen or $C_1$–$C_6$ alkyl;

said process comprising the steps of:

a) preparing a starting reagent of the general formula

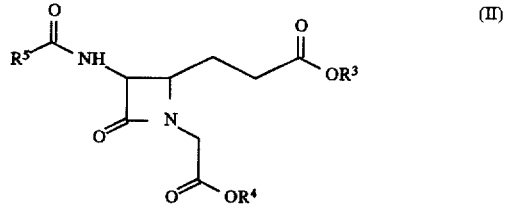

where $R^3$ is $C_1$–$C_6$ alkyl;

$R^4$ is an activated ester forming group; and $R^5$ is a protected amino acid;

b) preparing a mixture of a plurality of protected amino acids by tethering with a chemical linker individual protected amino acids to a solid support and then mixing said chemically linked protected amino acids in approximately equimolar concentrations;

c) mixing the mixture of said plurality of protected amino acids with the formula (II) starting reagent to form formula (III) intermediates:

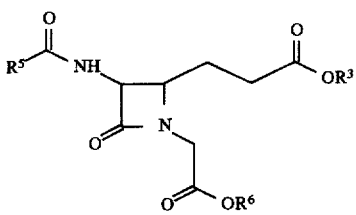
(III)

where $R^6$ is said mixture of a plurality of said protected amino acids;

d) deprotecting each of said $R^6$ protected amino acids; and e) mixing the mixture of said plurality of protected amino acids with the deprotected formula (III) intermediates to form a plurality of azetidinone analogs of formula (I).

2. The process of claim 1 wherein said solid support is a protected functionalized polymeric resin.

3. The process of claim 1 wherein step (b) includes the step of deprotecting the tethered protected amino acids prior to step (c).

4. The process of claim 2 wherein step (b) includes first adding the functionalized resin to a reaction vessel, then adding equimolar solutions of each protected amino acid to said reaction vessel, then agitating the reaction vessel.

5. The process of claim 1 wherein each individual protected amimo acid is a naturally occuring amino acid.

6. The process of claim 5 wherein each individual protected amino acid is a (D)-amino acid.

7. The process of claim 1 wherein individual protected amino acid is protected by a FMOC protecting group.

8. The process of claim 7 wherein step (d) includes deprotecting each amino acid with piperidine.

9. The process of claim 1 wherein each protected amino acid is selected from the group consisting of glycine, leucine, lysine, serine, glutamine, tryptophan, hydroxyproline, phenylalanine and alanine.

10. The process of claim 1 wherein $R^4$ is an activated ester forming group.

11. The process of claim 10 wherein $R^4$ is pentafluorophenyl.

12. The process of claim 1 and a further step (f) of adding another mixture a plurality of individual protected amino acids to the formula (I) compounds to form tri- and longer peptide chains at one or both of the $R^1$ and $R^2$ moieties.

13. The process of claim 1 and a step of capping each $R^1$ and $R^2$ moiety with a terminal amino group.

* * * * *